(12) United States Patent
Allen et al.

(10) Patent No.: US 7,259,731 B2
(45) Date of Patent: Aug. 21, 2007

(54) MEDICAL OVERLAY MIRROR

(75) Inventors: Paul G. Allen, Seattle, WA (US); Edward K. Y. Jung, Bellevue, WA (US); Royce A. Levien, Lexington, MA (US); Mark A. Malamud, Seattle, WA (US); John D. Rinaldo, Jr., Bellevue, WA (US)

(73) Assignee: Searete LLC, Bellevue, WA (US)

( * ) Notice: Subject to any disclaimer, the term of this patent is extended or adjusted under 35 U.S.C. 154(b) by 148 days.

(21) Appl. No.: 10/951,002

(22) Filed: Sep. 27, 2004

(65) Prior Publication Data

US 2006/0072798 A1   Apr. 6, 2006

(51) Int. Cl.
*G09G 3/00* (2006.01)
(52) U.S. Cl. .......................... 345/32; 345/156
(58) Field of Classification Search ............... 345/8, 345/156, 173, 32; 132/301; 382/154; 2/209.14; 434/371; D28/64.1; D03/275
See application file for complete search history.

(56) References Cited

U.S. PATENT DOCUMENTS

| | | | |
|---|---|---|---|
| 3,838,525 A | 10/1974 | Harvey | |
| 3,934,226 A | 1/1976 | Stone et al. | |
| 5,198,936 A | 3/1993 | Stringfellow | |
| 5,997,149 A | 12/1999 | Chu | |
| 6,032,119 A | 2/2000 | Brown et al. | |
| 6,071,236 A | 6/2000 | Iliff | |
| 6,095,985 A | 8/2000 | Raymond et al. | |
| 6,120,467 A | 9/2000 | Schallhorn | |
| 6,238,337 B1 | 5/2001 | Kambhatla et al. | |
| 6,272,468 B1 | 8/2001 | Melrose | |
| 6,322,502 B1 | 11/2001 | Schoenberg et al. | |
| 6,336,900 B1 | 1/2002 | Alleckson et al. | |
| 6,402,689 B1 | 6/2002 | Scarantino et al. | |
| 6,440,090 B1 | 8/2002 | Schallhorn | |
| 6,454,708 B1 | 9/2002 | Ferguson et al. | |
| 6,468,263 B1 | 10/2002 | Fischell et al. | |
| 6,516,210 B1 | 2/2003 | Foxall | |
| 6,542,204 B1 | 4/2003 | Ohzawa et al. | |
| 6,556,977 B1 | 4/2003 | Lapointe et al. | |
| 6,569,094 B2 | 5/2003 | Suzuki et al. | |
| 6,574,742 B1 | 6/2003 | Jamroga et al. | |
| 6,678,703 B2 | 1/2004 | Rothschild et al. | |
| 6,710,927 B2 | 3/2004 | Richards | |
| 6,725,200 B1 | 4/2004 | Rost | |
| 6,746,122 B2 | 6/2004 | Knox | |
| 6,755,539 B2 | 6/2004 | Brennesholtz | |
| 6,757,087 B1 | 6/2004 | Taketomi et al. | |
| 6,760,515 B1 | 7/2004 | Wang et al. | |

(Continued)

FOREIGN PATENT DOCUMENTS

JP          05181216 A2      7/1993

(Continued)

OTHER PUBLICATIONS

Azuma, Ronald; Baillot, Yohan; Behringer, Reinhold; Feiner, Steven; Julier, Simon; MacIntyre, Blair; "Recent Advances in Augmented Reality," pp. 34-47; located at www.cs.unc.edu/~azuma/cga2001.pdf; bearing a date of Nov./Dec. 2001; printed on Jul. 12, 2004.

(Continued)

*Primary Examiner*—Ricardo Osorio

(57) ABSTRACT

Medical overlay mirror methods and related systems.

38 Claims, 12 Drawing Sheets

U.S. PATENT DOCUMENTS

| | | | |
|---|---|---|---|
| 6,761,458 | B2 | 7/2004 | Sakata et al. |
| 6,762,870 | B2 | 7/2004 | De Vaan |
| 6,774,869 | B2* | 8/2004 | Biocca et al. .................. 345/8 |
| 2001/0031081 | A1* | 10/2001 | Quan et al. ................. 382/154 |
| 2001/0037191 | A1* | 11/2001 | Furuta et al. .................. 703/6 |
| 2002/0196333 | A1* | 12/2002 | Gorischek .................... 348/61 |
| 2003/0041871 | A1* | 3/2003 | Endo et al. ................. 132/301 |
| 2004/0095359 | A1 | 5/2004 | Simon et al. |
| 2005/0185278 | A1* | 8/2005 | Horsten et al. ............. 359/487 |

FOREIGN PATENT DOCUMENTS

| | | |
|---|---|---|
| JP | 06055957 A2 | 3/1994 |
| WO | WO 02/080773 A1 | 10/2002 |

OTHER PUBLICATIONS

Butz, Andreas; Beshers, Clifford; Feiner, Steven; "Of Vampire Mirrors and Privacy Lamps: Privacy Management in Multi-User Augmented Environments," pp. 171-172; located at http://www1.cs.columbia.edu/~butz/publications/papers/uist98.pdf; bearing a date of Nov. 2-4, 1998; printed on Jul. 12, 2004.

Computer Vision & Robotics Laboratory Beckman Institute, "Multiview Mirror Pyramid Panoramic Cameras," Tan, Kar-Han; Hua, Hong; Ahuja, Narendar from the Beckman Institute for Advanced Science and Technology, University of Illinois at Urbana-Champaign, pp. 1-4 located at http://vision.ai.uiuc.edu/~tankh/Camera/camera.html printed on Aug. 9, 2004.

Francois, Alexandre R.J.; Kang, Elaine; "The Virtual Mirror," pp. 1-5; located at http://iris.usc.edu/~afrancoi/virtual_mirror/; printed on Jul. 12, 2004.

Fulford, Benjamin, "Adventures in the Third Dimension" pp. 1-3 located at www.forbes.com/forbes/2004/0524/166_print.html bearing a date of May 24, 2004 and printed on Sep. 1, 2004.

Healthy Style Products, "Emjoi—The Mirror AP-13," pp. 1-2 located at http://www.healthstyleproducts.com/mirror.html printed on Sep. 1, 2004.

Highbeam Research; "Winntech. (Globalshop 2003 Spotlight);" pp. 1; located at http://www.highbeam.com/library/doc0.asp?docid=1G1:99048681&refid=ink_g5s1&skeyw; printed on Jul. 12, 2004.

Lin, I-Chen; Yeh, Jeng-Sheng; and Ouhyoung, Ming from National Taiwan University, "Extracting 3D Facial Animation Parameters from Multiview Video Clips," pp. 2-10, bearing a date of Nov./Dec. 2002 and printed on Sep. 1, 2004.

Lin, I-Chen, "The Software Tool of Mass 3D Facial Animation Parameter Extraction from Mirror-Reflected Multi-View Video User's Instruction Version 1.0," located at http://www.cmlab.csie.ntu.edu.tw/~ichen, pp. 1-24 (+ cover sheet), printed on Sep. 1, 2004.

Morimoto, Carlos Hitoshi; "Interactive Digital Mirror," from XIV Brazilian Symposium on Computer Graphics and Image Processing (SIBGRAPI'01), Oct. 15-18, 2001; pp. 1; located at http://csdl.computer.org/comp/proceeding/sibgrapi/2001/1330/00/13300232abs.htm; bearing a date of 2001; printed on Jul. 12, 2004.

Nextag, "Accessories—compare prices, review and buy at NexTag—Price—Review re Jerdon Mirror,"pp. 1-2 located at http://www.nextag.com/Jerdon_Accessories~2702144zJerdonz0zB36ozmainz5-htm printed on Sep. 1, 2004.

NP Review.Info, "New Product Reviews: New New Product Review—Jerdon JGL9W Magnification Tri-fold Lighted Mirror Product Review," pp. 1-3 located at http://www.npreview.info/Home-and-Garden/Home-Decor/Mirrors/Vanity-Mirrors/Jerdon-JGL9W-5X-Magnification-Tri-fold-Lighted-Mirror.html printed on Sep. 1, 2004.

Riviere, Cameron; Taylor, Russ; Digioia, A.; Wenz, J.; Kostuik, J.; Frassica, F.; "Engineered System Family #3: Information-enhanced Minimally Invasive Surgery," pp. 1-12; located at http://cisstweb.cs.jhu.edu/research/InfoEnhMIS/InfoEnhMISMain.htm; printed on Jul. 12, 2004.

Rochester Institute of Technology; "Introduction to Augmented Reality," pp. 1-12; located at http://www.se.rit.edu/~jrv/reserch/ar/introduction.html; printed on Jul. 12, 2004.

SIGGRAPH Emerging Technologies 1991-2002; "Interactive Paradigm, Technique," pp. 1-5; located at http://www.siggraph.org/~fujii/etech/s_interactive.html; bearing a date of Jul. 5, 2002; printed on Jul. 12, 2004.

SIGGRAPH Emerging Technologies 1991-2002; "Magic Morphin Mirror: Face-Sensitive Distortion and Exaggeration," pp. 1-2; located at http://siggraph.org./~jujii/etech/1997_190.html; bearing a date of Jul. 5, 2002; printed on Jul. 12, 2004.

Spohrer, J.C.; "Information in places," from vol. 38, allegedly of No. 4, 1999, Pervasive Computing; pp. 1-25; located at http://www.research.ibm.com/journal/sj/384/spohrer.html; printed on Jul. 12, 2004.

Sturm, Peter, "Mixing Catadioptric and Perspective Cameras," pp. 1-8, located at http://www.inrialpes.fr/movi/people/Sturm bearing a date of 2002 and printed on Sep. 1, 2004.

Tan, Kar-Han; Hua, Hong, Ahuja, Narenda "Multiview Panoramic Cameras Using Mirror Pyramids," accepted for publication in the IEEE Transactions on Pattern Analysis and Machine Intelligence journal, pp. 1-19 (+ cover sheet), printed on Sep. 1, 2004.

Taniguchi, Rin-Ichiro, "Real-Time Multiview Image Analysis and Its Application," pp. 1-8 printed on Sep. 1, 2004.

The Swiss Technorama Science Center, "Mirrors in Mind: Mirror, Mirror, on the Wall," pp. 1-12, located at http://www.technorama.ch/rentals/description.html printed on Sep. 1, 2004.

Traxtal; "What is Augmented Reality," pp. 1-2; located at http://www.traxtal.com/rd/rd_classroom_augmentedreality.htm; printed on Jul. 12, 2004.

Radford, Tim, "Mirror, Mirror on the Wall, Who'll Be Fattest of Them All?", The Guardian Unlimited, bearing a date of Feb. 3, 2005, pp. 1-4, located at http://www.guardian.co.uk/uk_news/story/0,3604,1404636.00.html, printed on Feb. 4, 2005.

PCT International Search Report; International App. No. PCT/US05/27410; Jan. 27, 2006.

PCT International Search Report; International App. No. PCT/US05/27250; May 2, 2006.

PCT International Search Report; International App. No. PCT/US05/27249; Apr. 21, 2006.

PCT International Search Report; International App. No. PCT/US05/27256; Apr. 21, 2006.

* cited by examiner

MEDICAL OVERLAY MIRROR

CROSS-REFERENCE TO RELATED APPLICATIONS

The present application is related to, claims the earliest available effective filing date(s) from (e.g., claims earliest available priority dates for other than provisional patent applications; claims benefits under 35 U.S.C. §119(e) for provisional patent applications), and incorporates by reference in its entirety all subject matter of the herein listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith. The United States Patent Office (USPTO) has published a notice to the effect that the USPTO's computer programs require that patent applicants reference both a serial number and indicate whether an application is a continuation or continuation in part. Stephen G. Kunin, *Benefit of Prior-Filed Application*, USPTO Electronic Official Gazette. Mar. 18, 2003 at http://www.uspto.gov/web/offices/com/sol/og/2003/week11/patbene.htm. The present applicant entity has provided below a specific reference to the application(s) from which priority is being claimed as recited by statute. Applicant entity understands that the statute is unambiguous in its specific reference language and does not require either a serial number or any characterization such as "continuation" or "continuation-in-part." Notwithstanding the foregoing, applicant entity understands that the USPTO's computer programs have certain data entry requirements, and hence applicant entity is designating the present application as a continuation in part of its parent applications, but expressly points out that such designations are not to be construed in any way as any type of commentary and/or admission as to whether or not the present application contains any new matter in addition to the matter of its parent application(s).

1. For purposes of the USPTO extra-statutory requirements, the present application constitutes a continuation in part of currently co-pending United States patent application entitled TIME-LAPSING MIRROR, naming Paul G. Allen, Edward K. Y. Jung, Royce A. Levien, Mark A. Malamud, and John D. Rinaldo, Jr. as inventors, U.S. application Ser. No. 10/910,421 filed Aug. 2, 2004.
2. For purposes of the USPTO extra-statutory requirements, the present application constitutes a continuation in part of currently co-pending United States patent application entitled COSMETIC ENHANCEMENT MIRROR, naming Paul G. Allen, Edward K. Y. Jung, Royce A. Levien, Mark A. Malamud, and John D. Rinaldo, Jr. as inventors, U.S. application Ser. No. 10/912,271 filed Aug. 5, 2004.
3. For purposes of the USPTO extra-statutory requirements, the present application constitutes a continuation in part of currently co-pending United States patent application entitled MULTI-ANGLE VIEW MIRROR, naming Edward K. Y. Jung, Royce A. Levien, Mark A. Malamud, and John D. Rinaldo, Jr. as inventors, U.S. application Ser. No. 10/941,803 filed Sep. 15, 2004.

TECHNICAL FIELD

The present application relates, in general, to mirror technologies.

SUMMARY

In one aspect, a system includes but is not limited to a light reflecting structure; a data presentation device proximate to said light reflecting structure; and a medical overlay engine operably couplable to said data presentation device. In addition to the foregoing, other system aspects are described in the claims, drawings, and text forming a part of the present application.

In one aspect, a system includes but is not limited to a light reflecting surface; an image representation capture device having an image field corresponding to said light reflecting surface; and at least one medical-overlaid image reception device operably couplable with said image representation capture device. In addition to the foregoing, other system aspects are described in the claims, drawings, and text forming a part of the present application.

In one aspect, a method includes but is not limited to accepting input related to at least a part of an image of a light reflecting structure; and presenting one or more medically-overlaid images related to at least a part of the image of the light reflecting structure. In addition to the foregoing, other method aspects are described in the claims, drawings, and text forming a part of the present application.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to: a digital mirror; a data presentation device proximate to said digital mirror; and a medical overlay engine operably couplable to said data presentation device. In addition to the foregoing, other system aspects are described in the claims, drawings, and text forming a part of the present application.

In addition to the foregoing, various other method and/or system aspects are set forth and described in the text (e.g., claims and/or detailed description) and/or drawings of the present application.

The foregoing is a summary and thus contains, by necessity, simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the detailed description set forth herein.

BRIEF DESCRIPTION OF THE FIGURES

The use of the same symbols in different drawings typically indicates similar or identical items.

DETAILED DESCRIPTION

Figure 1:
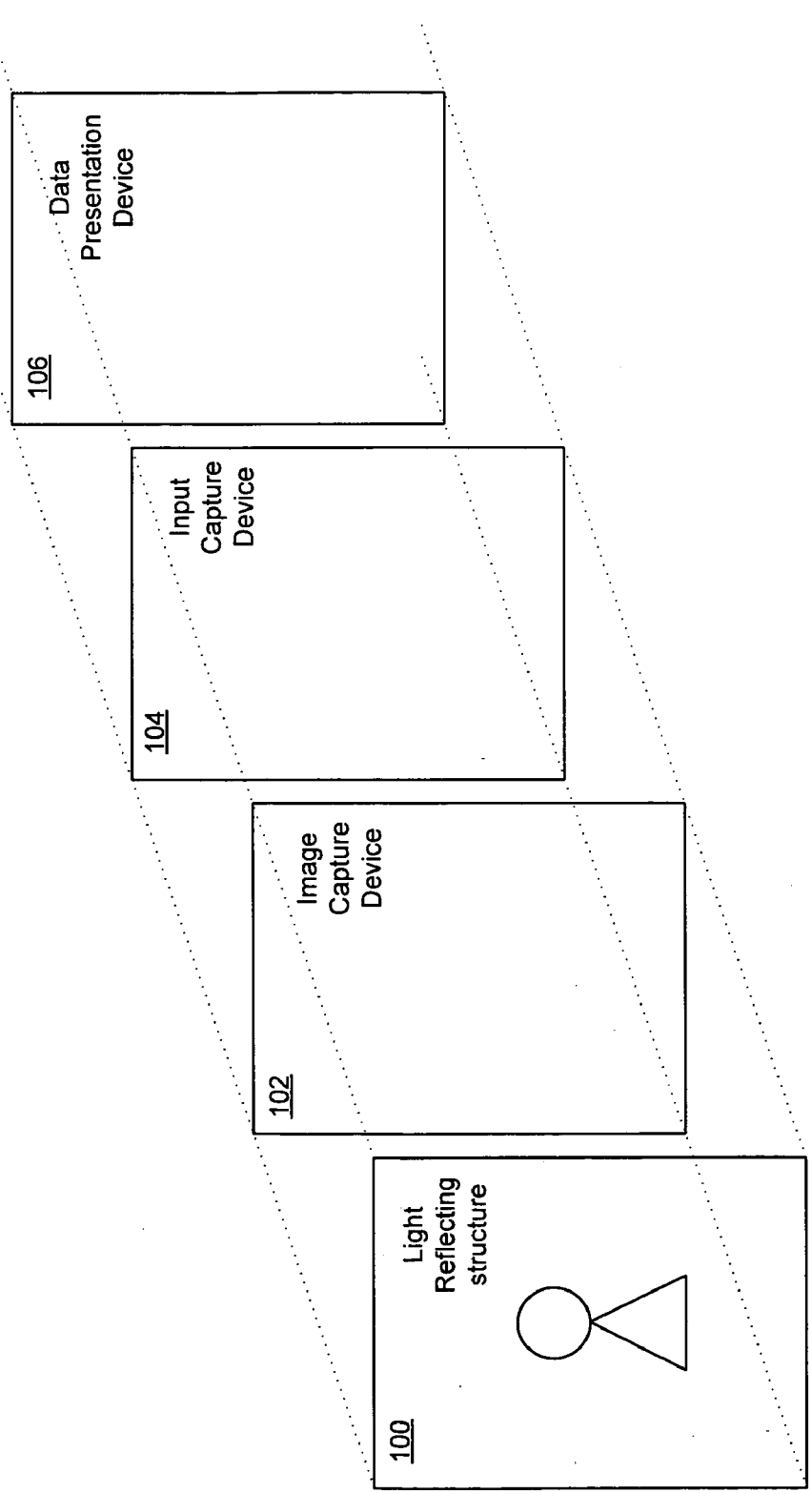
FIG. 1 shows a partial view of a system that may serve as an illustrative environment of and/or for subject matter technologies.

With reference to the figures, and with reference now to FIG. 1, shown is a partial view of a system that may serve as an illustrative environment of and/or for subject matter technologies. Depicted are light reflecting structure 100, image capture device 102, input capture device 104, and data presentation device 106. In one exemplary implementation, light reflecting structure 100 can be a plane mirror, a convex mirror, and/or a concave mirror. In another exemplary implementation, light reflecting structure 100 can be a partially silvered mirror. In some exemplary implementations, light reflecting structure 100 can be a physical mirror. In other exemplary implementations, light reflecting structure 100 can be a digital mirror and/or a projection mirror. In yet other implementations, light reflecting structure 100 can be a combination of one or more physical mirrors and/or one or more digital mirrors and/or one or more projection mirrors. In some implementations, data presentation device 106 may present various types of time-lapse information in addition or in the alternative to image information, such as height and/or weight information. In some implementations, presentations of information may be in the form of various modalities including but not limited to graphs, tables, audio (speech, music, sound), text, store-and-forward formats (e.g., email, voicemail, and/or simple message system mail at various reporting intervals, such as in a weekly digest format), database formats et cetera.

Continuing to refer to FIG. 1, illustrated is data presentation device 106 proximate to light reflecting structure 100. One exemplary implementation of data presentation device 106 proximate to light reflecting structure 100 includes but is not limited to data presentation device 106 integral with light reflecting structure 100. Another exemplary implementation of data presentation device 106 proximate to light reflecting structure 100 includes but is not limited to data presentation device 106 operably coupled with light reflecting structure 100 (e.g., as used herein, proximate may mean operationally proximate—able to work and interact together either directly or through intermediate components—as well as and/or in addition to physically proximate and/or mechanically proximate). Yet another exemplary implementation of data presentation device 106 proximate to light reflecting structure 100 includes but is not limited to data presentation device 106 in physical communication with light reflecting structure 100. One exemplary implementation of data presentation device 106 in physical communication with light reflecting structure 100 includes but is not limited to data presentation device 106 connected with a frame connected with said physical light reflecting structure 100. In some implementations, data presentation device 106 can be a light generation device (e.g., a plasma display and/or a liquid crystal display), an image presentation device (e.g., a direct projection to the eye retinal display), and/or a laser device (e.g., a laser diode device).

Figure 2:
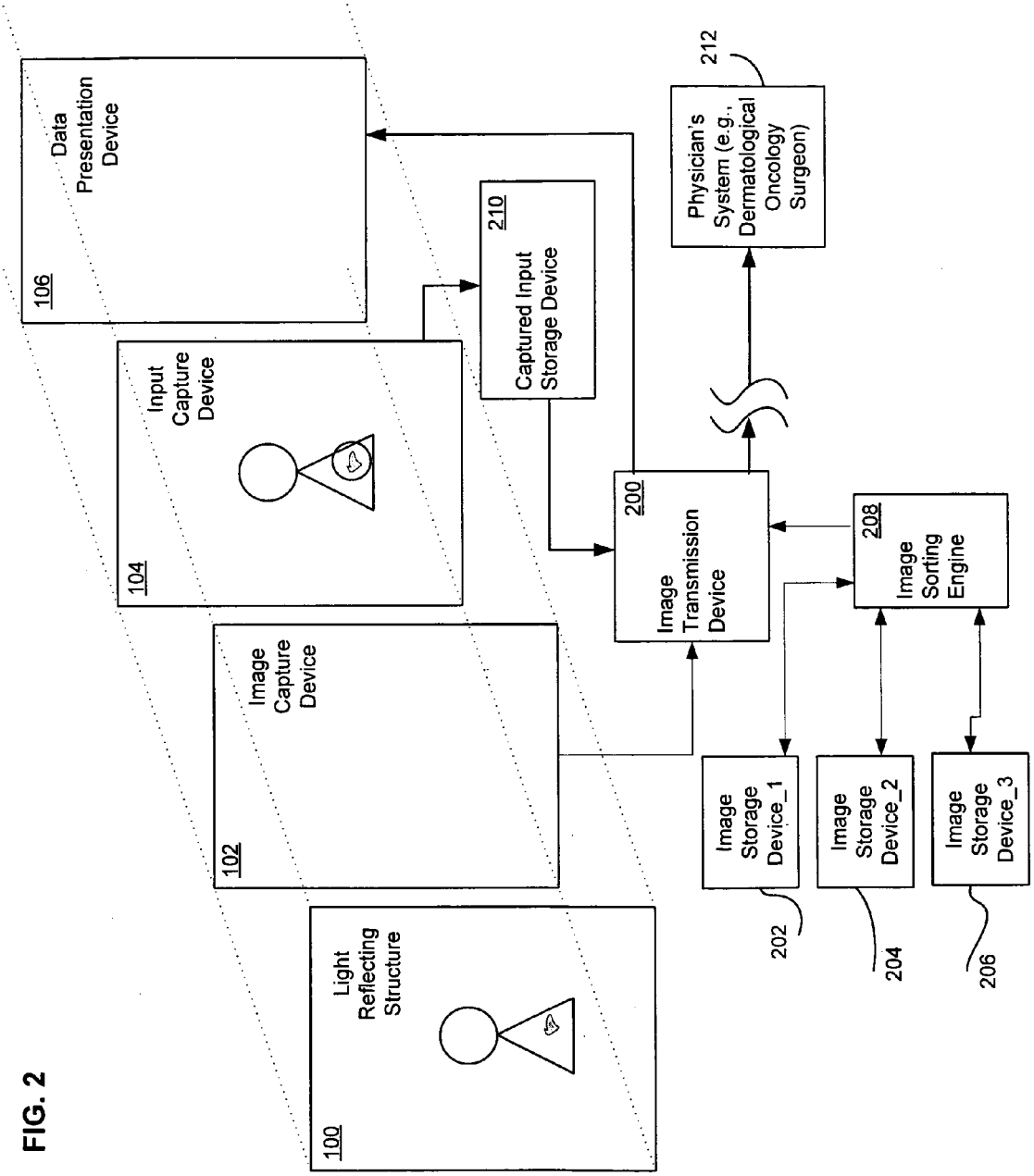
FIG. 2 depicts a partial view of a system that may serve as an illustrative environment of and/or for subject matter technologies.

Referring now to FIG. 2, depicted is a partial view of a system that may serve as an illustrative environment of and/or for subject matter technologies. Illustrated is that image transmission device 200 interfaces with image capture device 102. Shown is that image transmission device 200 interfaces—directly and/or indirectly—with image storage device_1 202, image storage device_2 204, image storage device_3 206, image sorting engine 208, captured input storage device 210, and physician's system 212. In one exemplary implementation, image transmission device 200 receives images from image capture device 102 and/or user input from captured input storage device 210 and/or input capture device 104. For example, as shown in FIG. 2, a user might submit to input capture device 104 that he desires to see medical data associated with an irregularly shaped dark lesion on his upper body. Thereafter, in one implementation, image transmission device 200 transmits one or more captured images and the user selected image regions for which medical overlay data is desired to physician's system 212. While physician's system 212 is described herein for sake of clarity, those skilled in the art will appreciate that physician's system 212 is merely exemplary of the more general case of a medical treatment participant. Examples of such medical treatment participants include but are not limited to persons/robots participating in generating medically-related correlations, medical expert systems, physicians (e.g., psychiatrists/psychologists), nutritionists, pharmacists., personal trainers, drug/chemical testing personnel, nurse practitioners, and/or parents or other people intimately associated with or involved in the medial assessment and diagnostic process (e.g., a parent working under the instructions of a medical caregiver, a delegate of medical professional, a medical treatment participant, someone using medical information (e.g., reading a medical paper), etc.).

In another implementation, image transmission device 200 transmits the one or more images and user selected image regions with respect to which medical data is desired to image sorting engine 208. Image sorting engine 208 thereafter sorts the received images into one or more of image storage device_1 202, image storage device_2 204, and image storage device_3 206 based on pattern recognition algorithms and stores the images in association with the user input. For example, in an implementation where image capture device 102 is capturing three-dimensional (3-D) images of a human subject, image sorting engine 208 may utilize 3-D image processing routines to sort various recognized captured images into image storage device_1 202, image storage device_2 204, and image storage device_3 206 (e.g., where images of a first person are sorted to image storage device_1 202, images of a second person are sorted to image storage device_2 204, and images of a third person are sorted to image storage device_3 206). Those skilled in the art will appreciate that, as used herein, sorting can include categorization, ordering, and/or other operations such as those described herein.

In yet another implementation, image transmission device 200 interacts with image sorting engine 208 to recall images from one or more of image storage device_1 202, image storage device_2 204, and image storage device_3 206 corresponding to an image in light reflecting structure 100. Thereafter, image transmission device 200 causes a display of those other retrieved images through data presentation device 106. Subsequently, a user may select, through the auspices of input capture device 104, one of those other retrieved images. Thereafter, the user may elect to send all or part of the selected images, along with all or part of his current image, to physician's system 212. For example, a user could send earlier images of his body wherein the dark lesion currently exists, along with his current image showing the current state of the lesion, to a dermatological oncologist in order to get an opinion from that oncologist based on a historical progression of the lesion.

Continuing to refer to FIG. 2, in one implementation, image capture device 102 can include at least one image representation device located to capture a field of view of light reflecting structure 100. For example, an active photo-detector array completely and/or partially in identity with a display portion of light reflecting structure 100 or a lensed image capture system oriented such that it can capture all or part of an image reflected from light reflecting structure 100. In another exemplary implementation, image capture device 102 can include at least two image representation devices located to capture a field of view of light reflecting structure 100. For example, two or more camera systems positioned to capture stereo imagery such that 3-D imaging techniques may be applied. The image capture devices described herein can be positioned substantially anywhere an image of light reflecting structure 100 can be captured, such as behind light reflecting structure 100 in order to catch transmitted images through a partially silvered mirror, to the sides and/or above and/or below a mirror, and/or positioned and/or oriented to the front of a mirror in order to record images reflected from a mirror.

Figure 3:
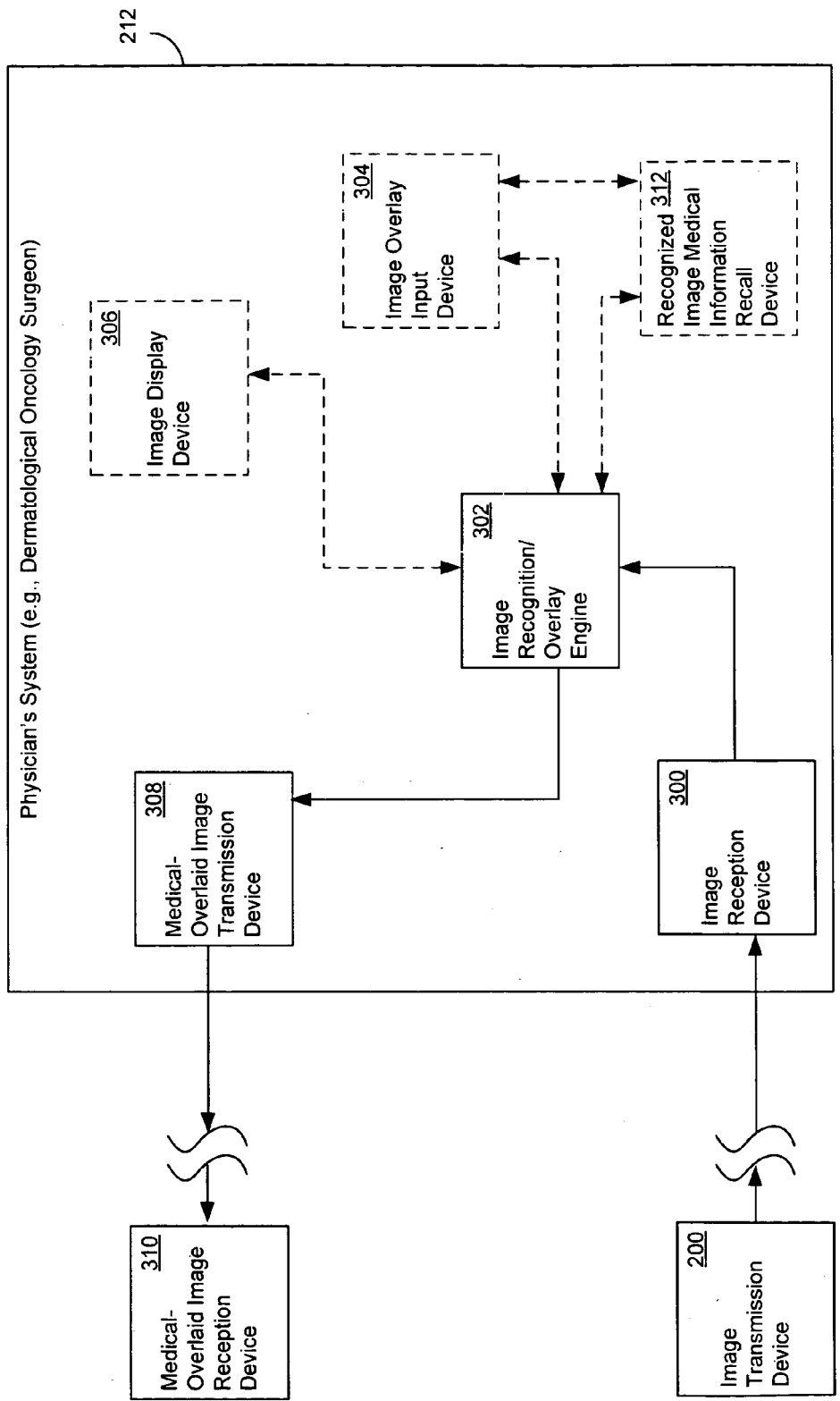
FIG. 3 illustrates a partial view of a system that may serve as an illustrative environment of and/or for subject matter technologies.

With reference now to FIG. 3, illustrated is a partial view of a system that may serve as an illustrative environment of and/or for subject matter technologies. Shown is image transmission device 200 in communication with image reception device 300. Depicted is image reception device 300 interfaced with image recognition/overlay engine 302. Illustrated is image recognition/overlay engine 302 interfaced with image overlay input device 304, image display device 306, and medical-overlaid image transmission device 308. Illustrated is medical-overlaid image transmission device 308 in communication with medical-overlaid image reception device 310.

In one exemplary implementation, image reception device 300 receives one or more images along with any associated user input(s) from image transmission device 200 (e.g., images with an indication that the user desires medical information associated with some portion of his body, face, arms, legs, etc. as such appear in one or more of the images). Thereafter, image reception device 300 transmits the received one or more images and any associated user input indicative of desired medical overlays to image recognition/ overlay engine 302. In one implementation, image recognition/overlay engine 302 causes a display of the one or more images and user input indicative of desired medical overlays on image display device 306 (e.g., a high-quality computer monitor).

Image overlay input device 304 accepts input (e.g., from a dermatological oncological surgeon) to overlay medical information onto the image of image display device 306. For instance, in one implementation image overlay input device 304 provides a graphical user interface and cursor driven input to allow a user (e.g., a dermatological oncological surgeon) to overlay the image of image display device 306 in accordance with user input. In response, image recognition/overlay engine 302 creates a medically overlaid version of the displayed image in accord with the input, and displays that medically overlaid image back to the surgeon through image display device 306 (often the medically overlaid image is displayed in tandem with the unmodified image). Thereafter, the surgeon indicates through image overlay input device 304 that the medically overlaid image is acceptable, and in response image recognition/overlay engine 302 causes medical-overlaid image transmission device 308 to transmit the image having the overlaid medical data back to medical-overlaid image reception device 310.

In another implementation, image recognition/overlay engine 302 uses pattern recognition logic to recognize Various medical conditions. Thereafter, image recognition/ overlay engine 302 transmits one or more images having the recognized medical condition to image overlay input device 304. At about the same time, image recognition/overlay engine 302 transmits the recognized medical condition to recognized image medical information recall device 312 which retrieves medical data in response to the recognized medical condition. Recognized medical information recall device 312 thereafter transmits the medical data to image overlay input device 304, which then overlays the medical data onto the one or more images in a programmed format and thereafter transmits the medically overlaid one or more images back to image recognition/overlay engine 302. Image recognition/overlay engine 302 then transmits the medically overlaid image as described previously.

Figure 4:
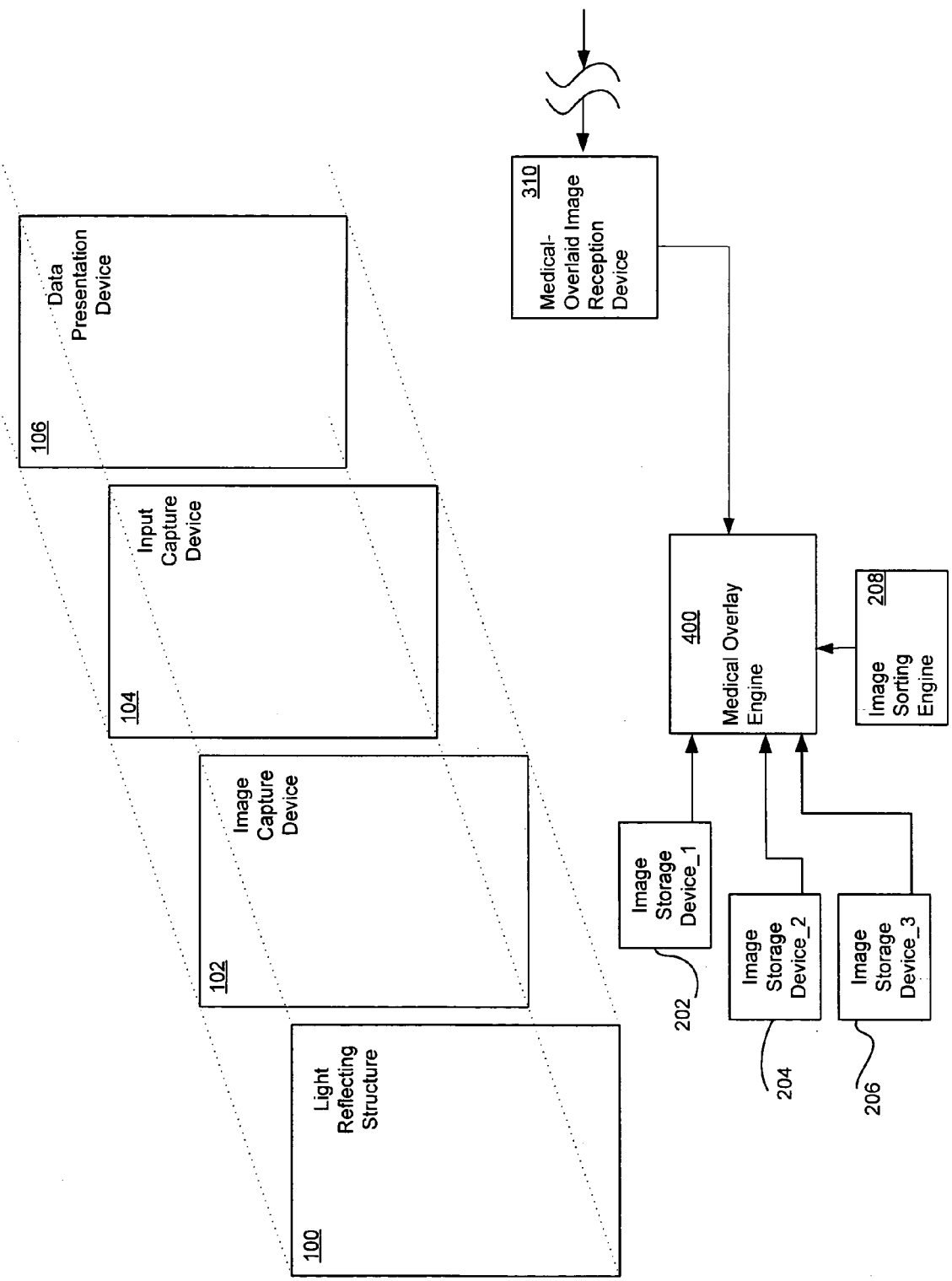
FIG. 4 illustrates a partial view of a system that may serve as an illustrative environment of and/or for subject matter technologies.

Referring now to FIG. 4, illustrated is a partial view of a system that may serve as an illustrative environment of and/or for subject matter technologies. Shown is medical-overlaid image reception device 310 receiving signals (e.g., such as those sent by medical-overlaid image transmission device 308 shown/described in relation to FIG. 3). Medical-overlaid image reception device 310 is shown interfaced with medical overlay engine 400. Medical overlay engine 400 is depicted interfacing with image sorting engine 208, image storage device_1 202, image storage device_2 204, and image storage device_3 206. Although medical overlay engine 400 is described in the context of overlaying physician and/or expert system generated overlay data, those having skill in the art will appreciate that medical data from other sources may also be overlaid, such as data from a bathroom scale, a diagnostic toilet, a blood pressure monitor, a diagnostic blood kit, etc., which are operably couplable with medical overlay engine 400. Other examples of medical data that may be overlaied can include but are not limited to current diagnostic readings (e.g., blood pressure, heartrate, blood sugar level, height, weight, cholesterol, etc.), historical diagnostic readings (average resting heart rate over time, average fasting blood sugar, trends in readings, etc.), automatic warnings about diagnostics (e.g., low blood sugar, high blood sugar, other protein analysis from urine, etc.), medication reminders such as including an ability to mark medication as taken and/or see historical compliances (e.g., flossed 30% of days in last month, took BP medication every day last week), medical reminders about injury rehabilitation (e.g., 10 leg lifts today for injured knee), workout program suggestions (e.g., pecs look good, do more triceps work), etc. In addition, in some implementations, medical overlay engine 400 includes a notification sub-engine (not shown) that provides for information can be pulled from an overlaying source as well as information being-pushed from an overlaying source.

In one implementation, medical overlay engine 400 receives one or more images with medical overlays from medical overlaid image reception device 310. In another implementation, in order to save time/bandwidth, medical-overlay engine 400 receives instructions as to how to modify the one or more images (e.g., by overlaying medical data onto the images), and medical-overlay engine 400 thereafter interacts with image sorting engine 208, image storage device_1 202, image storage device_2 204, and image storage device_3 206 to actually generate the medically-overlaid one or more images locally.

Figure 5:
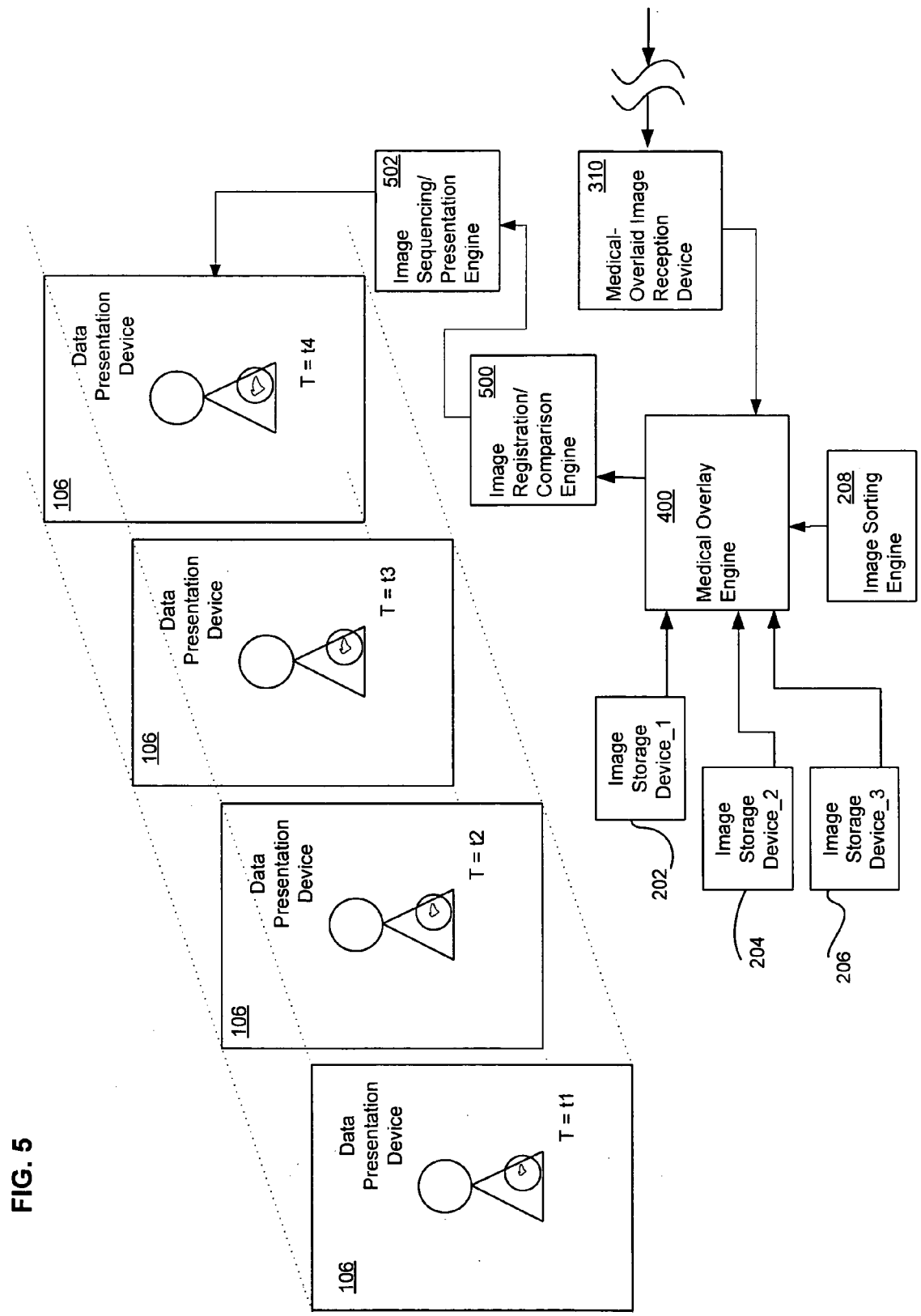
FIG. 5 shows a partial view of a system that may serve as an illustrative environment of and/or for subject matter technologies.

With reference now to FIG. 5, shown is a partial view of a system that may serve as an illustrative environment of and/or for subject matter technologies. Depicted is medical-overlay engine 400 interfaced with image registration/comparison engine 500. Shown is image registration/comparison engine 500 interfaced with image sequencing/presentation engine 502. In one exemplary implementation, medical-overlay engine 400—in concert with image sorting engine 208—retrieves one or more images from one or more of image storage device_1 202, image storage device_2 204, and image storage device_3 206. Subsequently, medical overlay engine 400 overlays medical data onto the one or more retrieved images in accord with received overlay instructions (e.g., such as those received from physician's system 212 as described herein). Thereafter, image registration/comparison engine 500 uses some relatively stable image feature(s), such as anatomical landmarks (e.g., bony regions or a center part of some defined anatomical feature, to encompass and or localize a region of interest where some feature of interest resides), to provide proper alignment amongst images and/or medical overlay data. In another implementation, medical overlay engine 400 receives images that have already been medically-overlaid by image recognition/overlay engine 302 of physician's system 212. Irrespective of whether the medically overlaid images are generated locally or received in already enhanced/modified form, in one implementation image sequencing/presentation engine 502 then presents the aligned images in a sequenced fashion such that the medically overlaid information produced responsive to the user input can be viewed. For instance, image sequencing/presentation engine 502 might present a sequenced presentation of various medical opinion/narratives with respect to various images of a skin lesion over time as supplied by a dermatological oncologist as described herein. In another implementation, image sequencing/presentation engine 502 presents a non-sequential menu of options, some which either entail and/or are related to various alternate proposed medical overlays from the dermatological oncologist.

Figure 6:
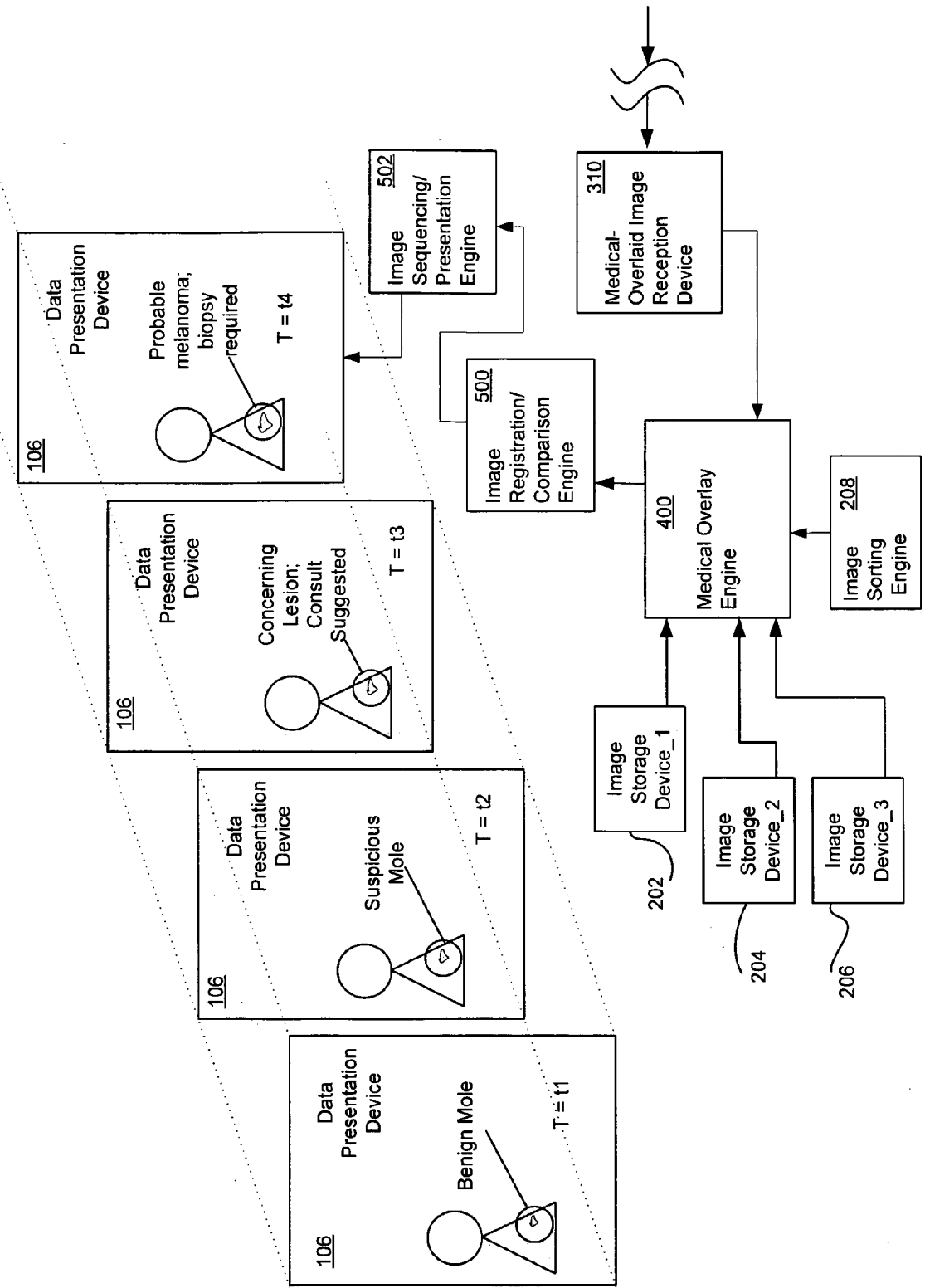
FIG. 6 depicts a partial view of a system that may serve as an illustrative environment of and/or for subject matter technologies

Referring now to FIG. 6, depicted is a partial view of a system that may serve as an illustrative environment of and/or for subject matter technologies. Illustrated is the system presenting four sequenced images showing various proposed medical overlays to a user's captured image. For instance, depicted at sequence time T=t1 is a presentation of an oldest image entered by the user/retrieved by the system as well as text indicative of a medical overlay. Specifically, shown is that the earliest image having a small irregularly shaped lesion has associated with it a medical overlay giving a doctor's opinion that the area of concern appears most like a benign mole (alternatively, in another contemplated implementation the medical opinion overlay is obtained from an electronic medical database searched with pattern recognition software). Like medical overlays to the user image are shown at sequence times T=t2 through T=t4. At sequence times T=t2 through T=t4, shown are various medical overlays onto the user's image in accord with the instructions of a dermatological oncologist such as described elsewhere herein. Depicted in FIG. 6 are exemplary overlays showing that the physician's opinion of the region over time is that the region has progressed from an apparent benign mole stage (T=t1), to a suspicious mole stage (T=t2), to a concerning skin lesion (T=t3), and ultimately to what superficially appears to be a probable melanoma (T=t4). Further shown in medical overlay are suggested courses of action to the patient (e.g., consult physician; obtain biopsy).

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations.

Figure 7:
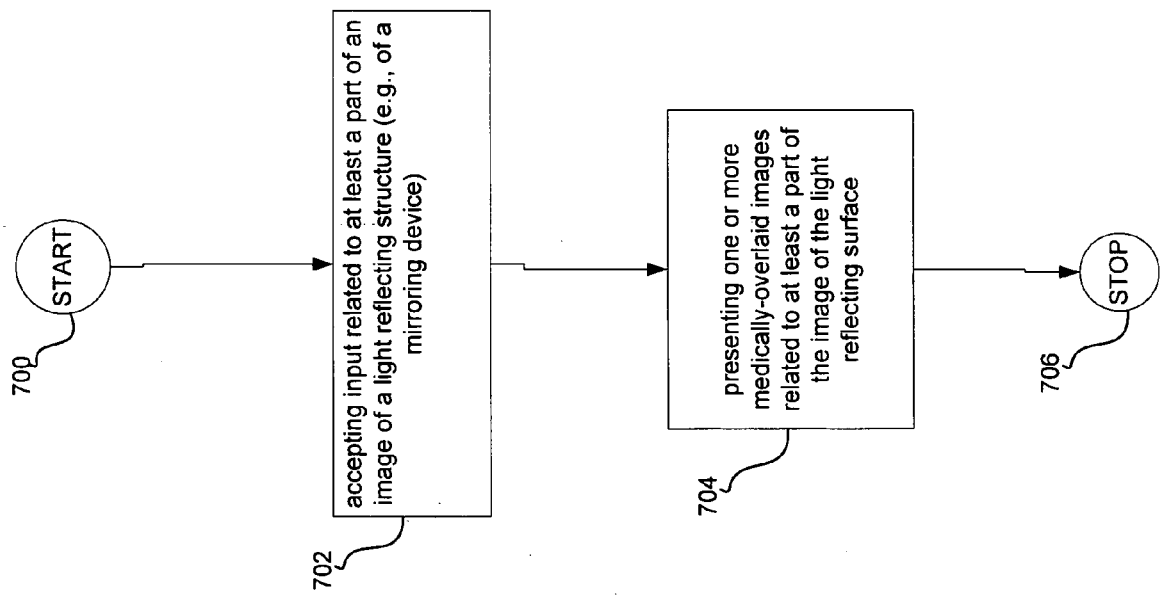
FIG. 7 illustrates a high-level logic flowchart of a process.

Referring now to FIG. 7, illustrated is a high-level logic flowchart of a process. Method step 700 shows the start of the process. Method step 702 shows accepting input related to at least a part of an image of a light reflecting structure (e.g., via input capture device 104 and/or captured input storage device 210 and/or a supporting component(s) accepting input when a user has indicated one or more portions of an image in light reflecting structure 100). Method step 704 depicts presenting one or more medically-overlaid images related to at least a part of the image of the light reflecting structure (e.g., such as shown/described in relation to FIG. 6). Method step 706 shows the end of the process. Those skilled in the art will appreciate that, in some implementations, the "at least a part of the image" can include but is not limited to a recognized region of an image or a recognized anchor point associated with an image which will provide the ability to do presentation on regions that both are and are not readily visually coordinated with an original field of view of a mirror. For example, in a hand-held mirror implementation, a user might zoom in on a region of an image and then ask to see a medically overlaid time-lapse sequence of images representative of changes in that zoomed-in region, such that the zoomed-in region is not readily visually coordinated with the original unzoomed field of view of the mirror. The inventors point out that those skilled in the art will appreciate that while the zoomed-in region might not be easily visually coordinated with the un-zoomed field of view, in some implementations the use of anchor points will allow coordination between the zoomed and unzoomed views. In addition, the inventors further point out that while examples set forth herein focus on anatomy and/or anatomical change for sake of clarity, the systems described herein can actually track and/or show a medically-overlaid time lapse of substantially any object that may be reflected in the mirror.

Figure 8:
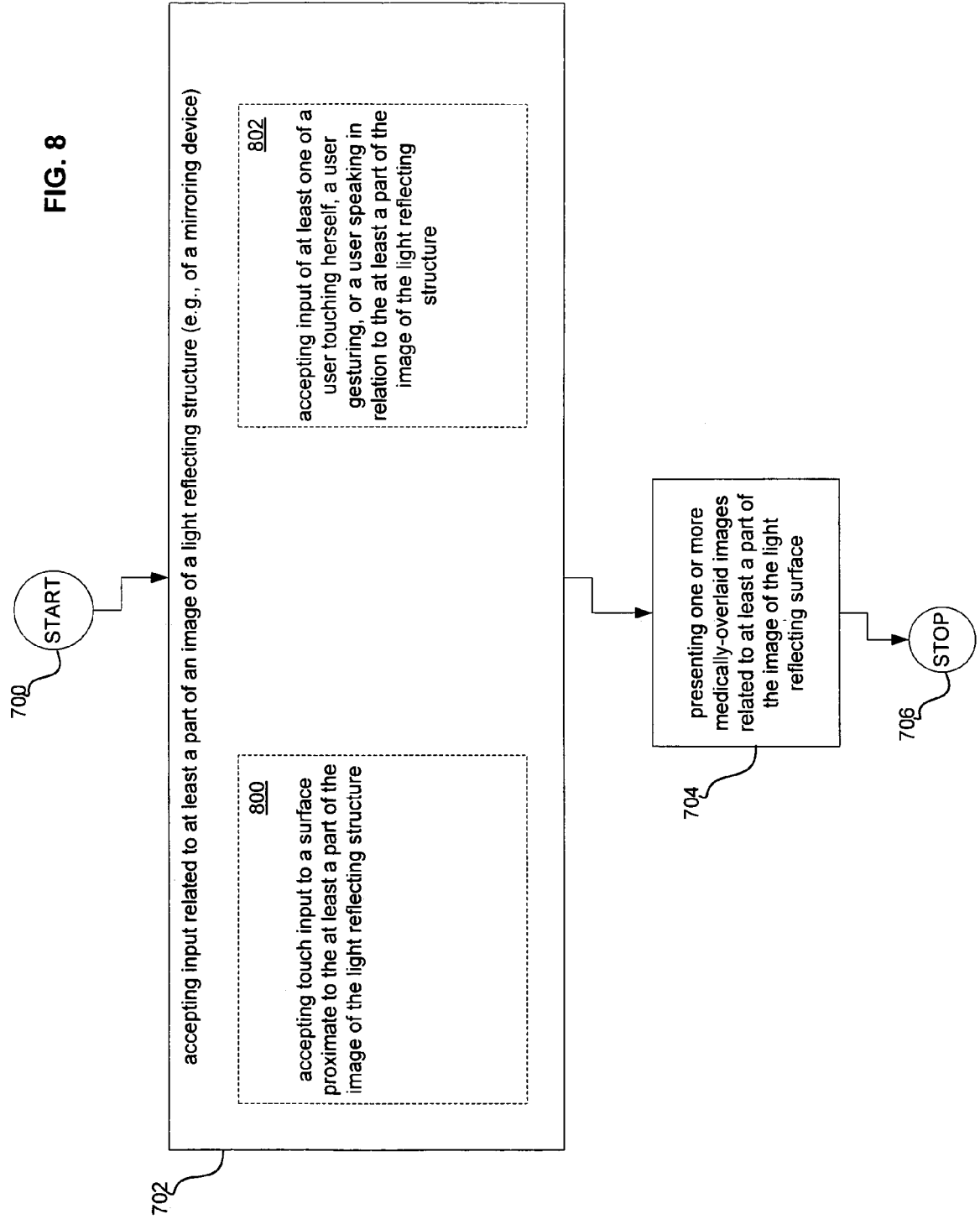
FIG. 8 shows a high-level logic flowchart depicting alternate implementations of the high-level logic flowchart of FIG. 7.

With reference now to FIG. 8, shown is a high-level logic flowchart depicting alternate implementations of the high-level logic flowchart of FIG. 7. Depicted is that in various alternate implementations, method step 702 includes method step 800 and/or method step 802. Method step 800 shows accepting touch input to a surface proximate to the at least a part of the image of the light reflecting structure (e.g., via input capture device 104 and/or captured input storage device 210 capturing input when a user has indicated one or more portions of an image in light reflecting structure 100). Method step 802 depicts accepting input of at least one of a user touching herself, a user gesturing, or a user speaking in relation to the at least a part of the image of the light reflecting structure For example, via input capture device 104 capturing input when a user's gestures or pointing relative to at least a part of an image in light reflecting structure 100 and/or the user speaking a command in relation to at least a part of an image in light reflecting structure 100. Specific examples of the foregoing would include a user leaning a body part toward light reflecting structures 100 and/or a user moving a body part into a field of view of light reflecting structure 100 (or vice versa), such as an input of moving a hand-held mirror over a location where the action of the movement itself coupled with the content of the image captured constitutes an input with respect to the image (e.g., a feature recognized in the image could constitute all or part of the input).

Figure 9:
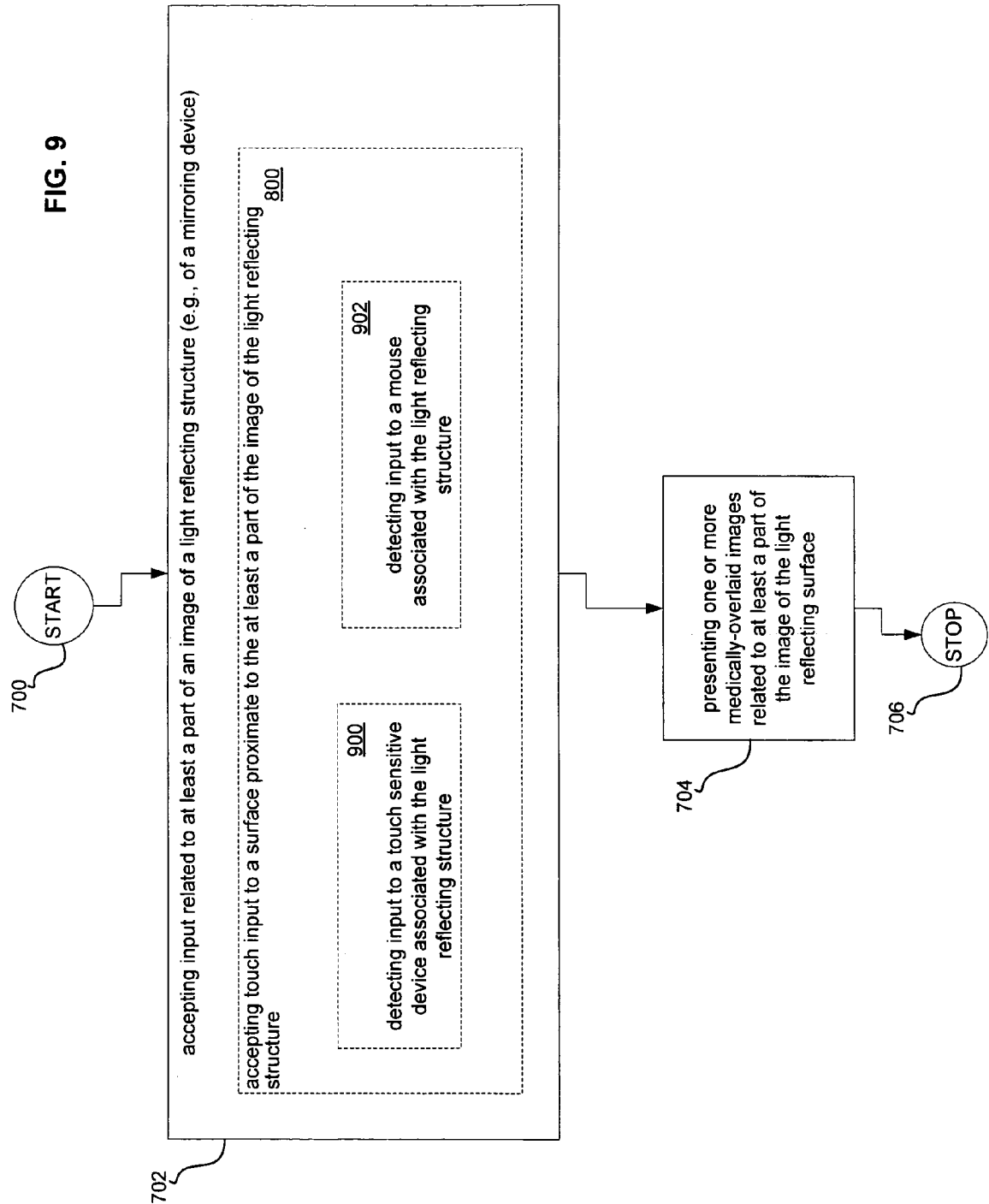
FIG. 9 depicts a high-level logic flowchart depicting alternate implementations of the high-level logic flowchart of FIG. 8.

Referring now to FIG. 9, depicted is a high-level logic flowchart depicting alternate implementations of the high-level logic flowchart of FIG. 8. Depicted is that in one alternate implementation, method step 800 includes method step 900 and/or method step 902. Method step 900 shows detecting input to a touch sensitive device associated with the light reflecting structure (e.g. via light reflecting structure 100 and/or input capture device 104 and/or captured input storage device 210 and/or one or more of their supporting components). Method step 902 depicts detecting input to a mouse associated with the light reflecting structure (e.g. via light reflecting structure 100 and/or input capture device 104 and/or captured input storage device 210 and/or one or more of their supporting components).

Figure 10:
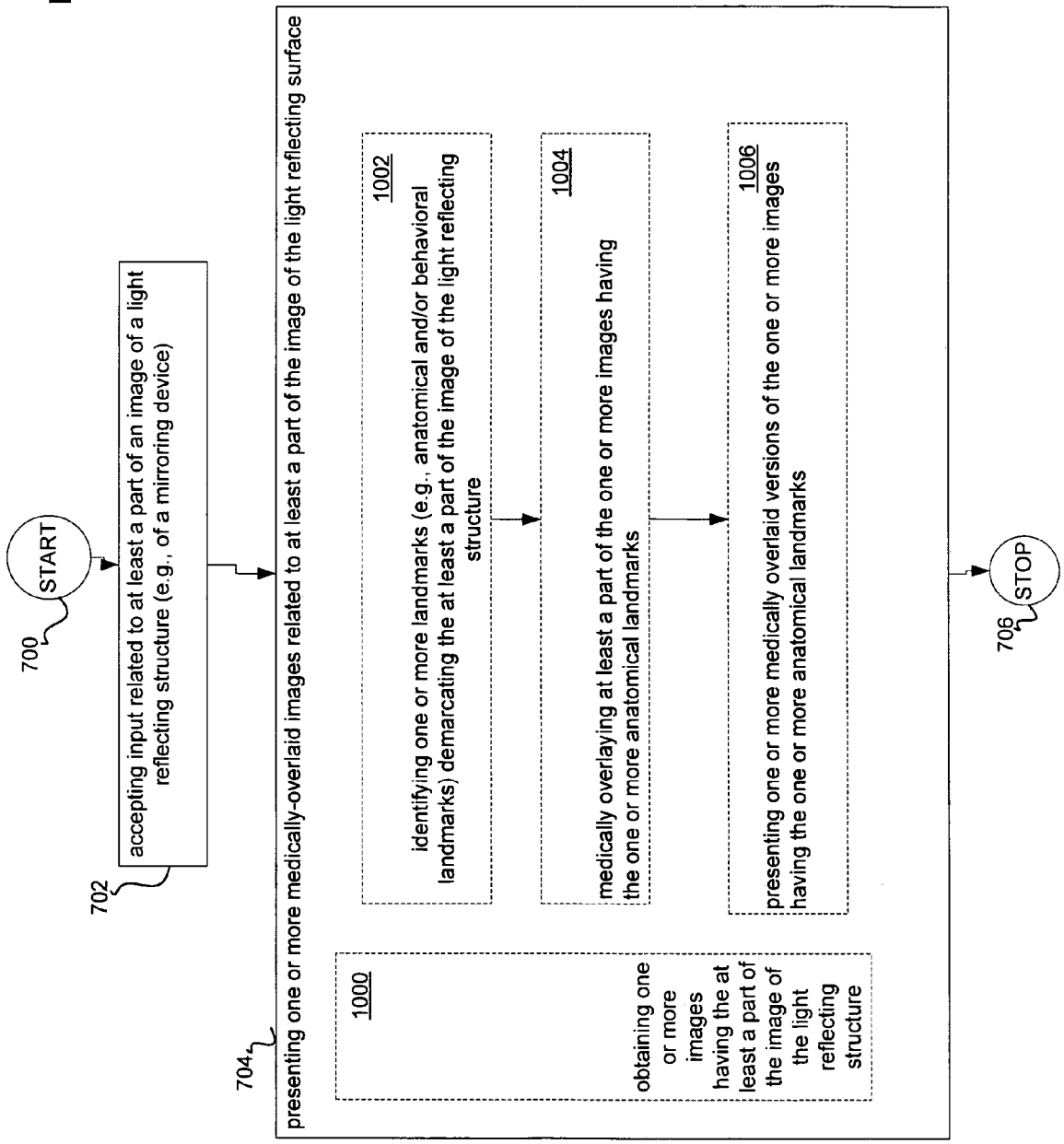
FIG. 10 illustrates a high-level logic flowchart depicting alternate implementations of the high-level logic flowchart of FIG. 7.

With reference now to FIG. 10, illustrated is a high-level logic flowchart depicting alternate implementations of the high-level logic flowchart of FIG. 7. Depicted is that in various alternate implementations, method step 704 includes method step 1000, and/or method steps 1002–1006. Method step 1000 shows one alternate implementation of obtaining one or more images having the at least a part of the image of the light reflecting structure. For example, obtaining the one or more images via image recognition/overlay engine 302, medical overlay engine 400, image sorting engine 208, and/or one or more of image storage devices 202–206.

Continuing to refer to FIG. 10, method steps 1002–1006 depict another alternate embodiment. Method step 1002 illustrates identifying one or more landmarks demarcating the at least a part of the image of the light reflecting structure (e.g., via image sorting engine 208 and/or image registration/comparison engine 500). Example of such landmarks include anatomical landmarks such as those described elsewhere herein and/or behavioral landmarks such as those associated with certain conditions such as physical and/or mental illness (e.g., facial expressions, skin tones, body positions/postures, etc.). Method step 1004 shows medically overlaying at least a part of the one or more images having the one or more landmarks (e.g., via image recognition/ overlay engine 302 and/or medical overlay engine 400). Method step 1006 depicts presenting one or more medically overlaid versions of the one or more images having the one or more landmarks (e.g., via data presentation device 106 and/or medical overlay engine 400).

Figure 11:
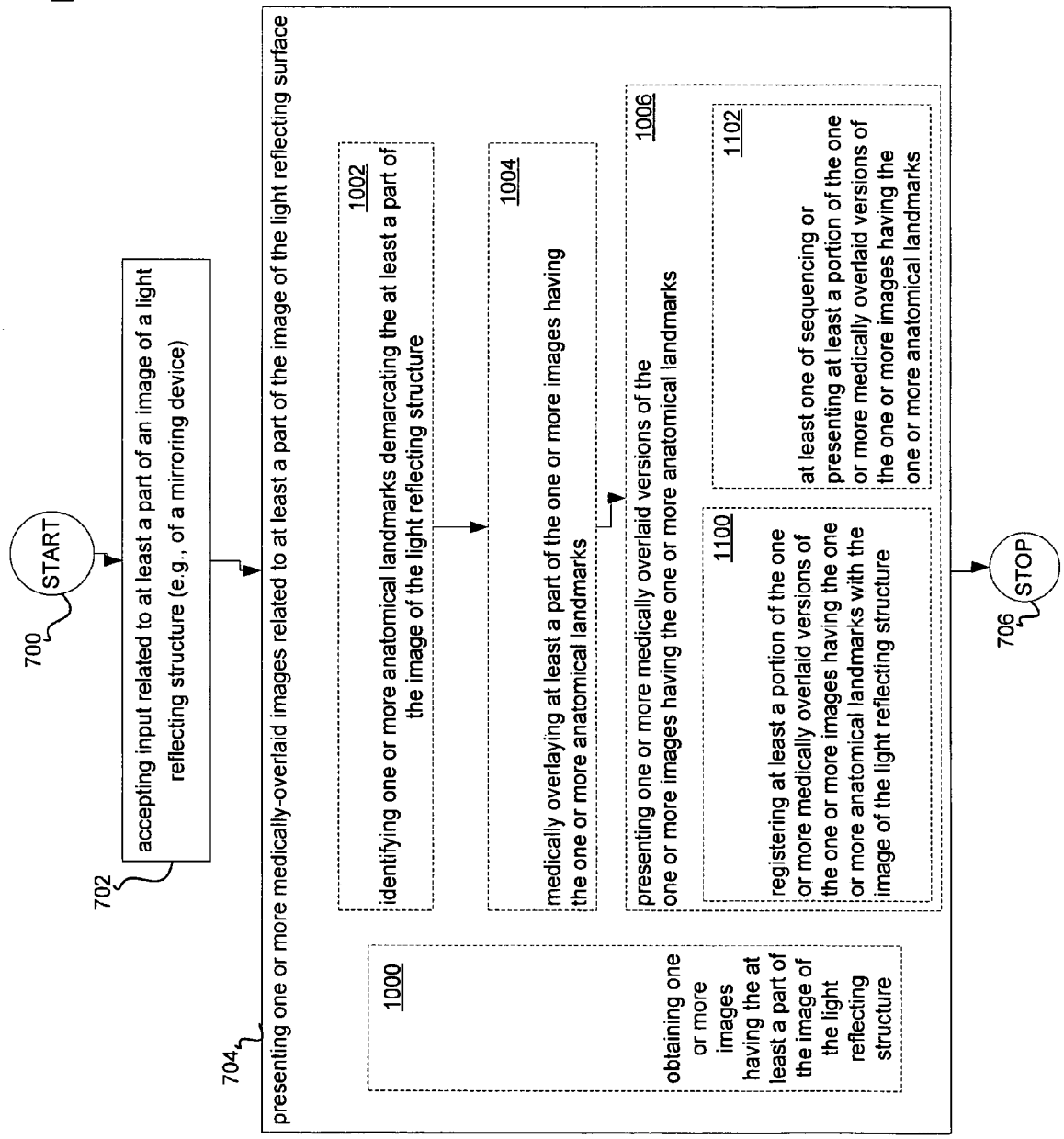
FIG. 11 shows a high-level logic flowchart depicting alternate implementations of the high-level logic flowchart of FIG. 10.

Referring now to FIG. 11, shown is a high-level logic flowchart depicting alternate implementations of the high-level logic flowchart of FIG. 10. Depicted is that in various alternate implementations, method step 1006 includes method step 1100 and/or method step 1102. Method step 1100 illustrates registering at least a portion of the one or more medically overlaid versions of the one or more images having the one or more landmarks with the image of the light reflecting structure (e.g., via image registration/comparison engine 500). Method step 1102 shows at least one of sequencing or presenting at least a portion of the one or more medically overlaid versions of the one or more images having the one or more landmarks (e.g., via image sequencing/presentation engine 502).

Figure 12:
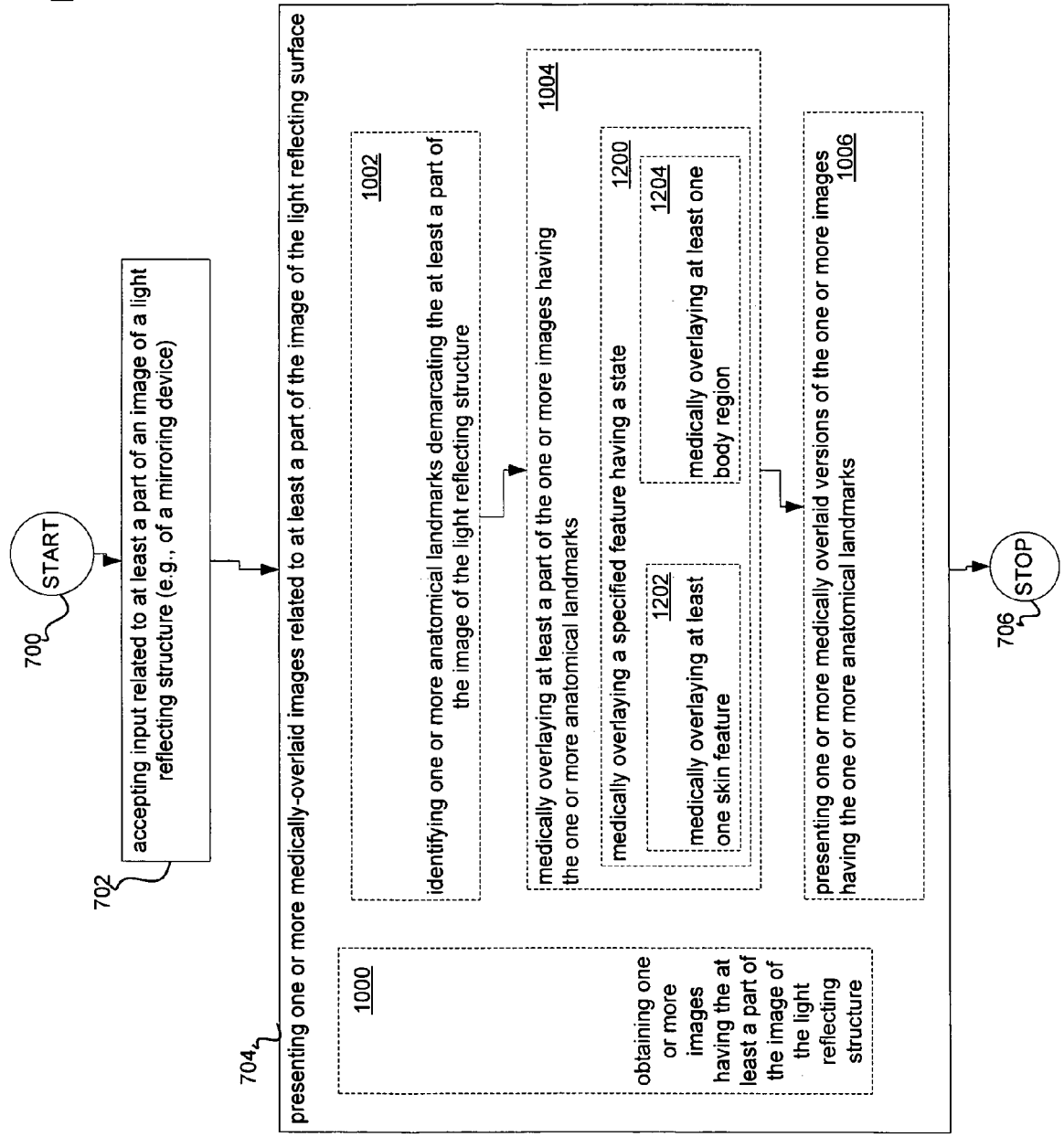
FIG. 12 illustrates a high-level logic flowchart depicting several alternate implementations of the high-level logic flowchart of FIG. 10.

Referring now to FIG. 12, illustrated is a high-level logic flowchart depicting several alternate implementations of the high-level logic flowchart of FIG. 10. Shown is that in one alternate implementation, method step 1004 includes method step 1200. Method step 1200 shows medically overlaying a specified feature having a state (e.g., via input capture device 102 and/or image recognition/overlay engine 302 and/or medical overlay engine 400 and/or their supporting components). Further shown is that in one alternate embodiment method stop 1200 can include method step 1202 which depicts medically overlaying at least one skin feature (e.g., placing text showing a medical opinion in proximity to a skin lesion, should a user have indicated that the skin region was of interest). Further shown is that in yet another alternate embodiment method stop 1200 can include method step 1204 which illustrates medically overlaying at least one body region (e.g., placing medical encyclopedia text/pictures in proximity to a rash on a person's torso, should the person have entered input indicating that the torso rash was of interest).

Those having skill in the art will appreciate that in some instances, the devices described herein can be networked. For example, having two or more of the mirroring devices described herein within a house that share their data between each other and/or having portable mirrors for use when traveling that can access data from mirrors in ones house. In addition, in other contemplated implementations the mirroring devices include notification sub-engines as described here and elsewhere that ensure that information can be pulled and/or pushed).

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter subject matter described herein applies regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

All of the above U.S. patents, U.S. patent application publications, U.S. patent applications, foreign patents, foreign patent applications and non-patent publications referred to in this specification and/or listed in any Application Data Sheet are incorporated herein by reference, in their entireties.

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components.

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together, etc.).

The invention claimed is:

1. A method comprising:
accepting input related to at least a part of an image in a light reflecting structure; and
presenting one or more medically-overlaid images related to at least a part of the image in the light reflecting structure, wherein said presenting one or more medically-overlaid images related to at least a part of the image in the light reflecting structure further comprises:
identifying one or more landmarks demarcating the at least a part of the image in the light reflecting structure;
medically overlaying at least a part of one or more images having the one or more landmarks; and
presenting one or more medically overlaid versions of the one or more images having the one or more landmarks.

2. The method of claim 1, wherein said accepting input related to at least a part of an image in a light reflecting structure further comprises:
accepting touch input to a surface proximate to the at least a part of the image in the light reflecting structure.

3. The method of claim 2, wherein said accepting touch input to a surface proximate to the at least a part of the image in the light reflecting structure further comprises:
detecting input to a touch sensitive device associated with the light reflecting structure.

4. The method of claim 2, wherein said accepting touch input to a surface proximate to the at least a part of the image in the light reflecting structure further comprises:
detecting input to a mouse associated with the light reflecting structure.

5. The method of claim 1, wherein said accepting input related to at least a part of an image in a light reflecting structure further comprises:
accepting input of at least one of a user touching herself, a user gesturing, or a user speaking in relation to the at least a part of the image in the light reflecting structure.

6. The method of claim 1, wherein said presenting one or more medically-overlaid images related to at least a part of the image in the light reflecting structure further comprises:
obtaining one or more images having the at least a part of the image in the light reflecting structure.

7. The method of claim 1, wherein said identifying one or more landmarks demarcating the at least a part of the image in the light reflecting structure further comprises:
identifying one or more anatomical landmarks.

8. The method of claim 1, wherein said identifying one or more landmarks demarcating the at least a part of the image in the light reflecting structure further comprises:
identifying one or more behavioral landmarks.

9. The method of claim 1, wherein said presenting one or more medically overlaid versions of the one or more images having the one or more landmarks further comprises:
registering at least a portion of the one or more medically overlaid versions of the one or more images having the one or more landmarks with the image in the light reflecting structure.

10. The method of claim 1, wherein said presenting one or more medically overlaid versions of the one or more images having the one or more landmarks further comprises:
at least one of sequencing or presenting at least a portion of the one or more medically overlaid versions of the one or more images having the one or more landmarks.

11. The method of claim 1, wherein said presenting one or more medically overlaid versions of the one or more images having the one or more landmarks further comprises:
presenting in a store and forward format.

12. The method of claim 1, wherein said presenting one or more medically overlaid versions of the one or more images having the one or more landmarks further comprises:
presenting in a database format.

13. The method of claim 1, wherein said medically overlaying at least a part of the one or more images having the one or more landmarks further comprises:
medically overlaying a specified feature having a state.

14. The method of claim 13, wherein said medically overlaying a specified feature having a state further comprises:
medically overlaying at least one skin feature.

15. The method of claim 13, wherein said medically overlaying a specified feature having a state further comprises:
medically overlaying at least one body region.

16. The method of claim 1, wherein said medically overlaying at least a part of one or more images having the one or more landmarks further comprises:
receiving at least one medical overlay of the at least a part of the one or more images having the one or more landmarks.

17. The method of claim 1, wherein said medically overlaying at least a part of one or more images having the one or more landmarks further comprises:
receiving at least one instruction of how to modify the at least a part of the one or more images having the one or more landmarks.

18. The method of claim 1, wherein said medically overlaying at least a part of one or more images having the one or more landmarks further comprises:
overlaying medical data relative to the at least a part of the one or more images having the one or more landmarks.

19. The method of claim 1, wherein said identifying one or more landmarks demarcating the at least a part of the image in the light reflecting structure further comprises:
receiving at least one part of an image having at least one identified landmark demarcating the at least a part of the image in the light reflecting structure.

20. A system comprising:
means for accepting input related to at least a part of an image in a light reflecting structure; and
means for presenting one or more medically-overlaid images related to at least a part of the image in the light reflecting structure, wherein said means for presenting one or more medically-overlaid images related to at least a part of the image in the light reflecting structure further comprises:
means for identifying one or more landmarks demarcating the at least a part of the image in the light reflecting structure;
means for medically overlaying at least a part of one or more images having the one or more landmarks; and
means for presenting one or more medically overlaid versions of the one or more images having the one or more landmarks.

21. The system of claim 20, wherein said means for accepting input related to at least a part of an image in a light reflecting structure further comprises:
means for accepting touch input to a surface proximate to the at least a part of the image in the light reflecting structure.

22. The system of claim 21, wherein said means for accepting touch input to a surface proximate to the at least a part of the image in the light reflecting structure further comprises:
means for detecting input to a touch sensitive device associated with the light reflecting structure.

23. The system of claim 21, wherein said means for accepting touch input to a surface proximate to the at least a part of the image in the light reflecting structure further comprises:
means for detecting input to a mouse associated with the light reflecting structure.

24. The system of claim 20, wherein said means for accepting input related to at least a part of an image in a light reflecting structure further comprises:
means for accepting input of at least one of a user touching herself, a user gesturing, or a user speaking in relation to the at least a part of the image in the light reflecting structure.

25. The system of claim 20, wherein said means for presenting one or more medically-overlaid images related to at least a part of the image in the light reflecting structure further comprises:
means for obtaining one or more images having the at least a part of the image in the light reflecting structure.

26. The system of claim 20, wherein said means for identifying one or more landmarks demarcating the at least a part of the image in the light reflecting structure further comprises:
means for identifying one or more anatomical landmarks.

27. The system of claim 20, wherein said means for identifying one or more landmarks demarcating the at least a part of the image in the light reflecting structure further comprises:
means for identifying one or more behavioral landmarks.

28. The system of claim 20, wherein said means for presenting one or more medically overlaid versions of the one or more images having the one or more landmarks further comprises:
means for registering at least a portion of the one or more medically overlaid versions of the one or more images having the one or more landmarks with the image in the light reflecting structure.

29. The system of claim 20, wherein said means for presenting one or more medically overlaid versions of the one or more images having the one or more landmarks further comprises:
means for at least one of sequencing or presenting at least a portion of the one or more medically overlaid versions of the one or more images having the one or more landmarks.

30. The system of claim 20, wherein said means for presenting one or more medically overlaid versions of the one or more images having the one or more landmarks further comprises:
means for presenting in a store and forward format.

31. The method of claim 20, wherein said means for presenting one or more medically overlaid versions of the one or more images having the one or more landmarks further comprises:
means for presenting in a database format.

32. The system of claim 20, wherein said means for medically overlaying at least a part of one or more images having the one or more landmarks further comprises:
means for medically overlaying a specified feature having a state.

33. The system of claim 32, wherein said means for medically overlaying a specified feature having a state further comprises:
means for medically overlaying at least one skin feature.

34. The system of claim 32, wherein said means for medically overlaying a specified feature having a state further comprises:
means for medically overlaying at least one body region.

35. The system of claim 20, wherein said means for medically overlaying at least a part of one or more images having the one or more landmarks further comprises:
means for receiving at least one medical overlay of the at least a part of the one or more images having the one or more landmarks.

36. The system of claim 20, wherein said means for medically overlaying at least a part of one or more images having the one or more landmarks further comprises:
means for receiving at least one instruction of how to modify the at least a part of the one or more images having the one or more landmarks.

37. The system of claim 20, wherein said means for medically overlaying at least a part of one or more images having the one or more landmarks further comprises:

means for overlaying medical data relative to the at least a part of the one or more images having the one or more landmarks.

38. The system of claim 20, wherein said means for identifying one or more landmarks demarcating the at least a part of the image in the light reflecting structure further comprises:

means for receiving at least one part of an image having at least one identified landmark demarcating the at least a part of the image in the light reflecting structure.

* * * * *

UNITED STATES PATENT AND TRADEMARK OFFICE
CERTIFICATE OF CORRECTION

PATENT NO. : 7,259,731 B2  
APPLICATION NO. : 10/951002  
DATED : August 21, 2007  
INVENTOR(S) : Paul G. Allen et al.

Page 1 of 1

It is certified that error appears in the above-identified patent and that said Letters Patent is hereby corrected as shown below:

Column 14, line 56, at claim 13 "at least a part of the one or more" should read --at least a part of one or more--

Signed and Sealed this
Eighteenth Day of December, 2012

David J. Kappos
*Director of the United States Patent and Trademark Office*